United States Patent [19]

Schmalfuss et al.

[11] Patent Number: 4,841,139

[45] Date of Patent: Jun. 20, 1989

[54] METHOD FOR TESTING COMPONENTS OF TRANSPARENT MATERIAL FOR SURFACE IRREGULARITIES AND OCCLUSIONS

[75] Inventors: Harald Schmalfuss, Rodgau; Hubert Kurpiella, Eschborn; Bernhard Schneider, Hofheim, all of Fed. Rep. of Germany

[73] Assignee: Battelle-Institut e.V., Frankfurt am Main, Fed. Rep. of Germany

[21] Appl. No.: 62,181

[22] Filed: Jun. 15, 1987

[30] Foreign Application Priority Data

Jun. 14, 1986 [DE] Fed. Rep. of Germany ....... 3620146

[51] Int. Cl.⁴ .............................................. G01N 9/04
[52] U.S. Cl. .................................. 250/223 R; 356/239
[58] Field of Search .................... 250/223 R; 356/237, 356/239

[56] References Cited

U.S. PATENT DOCUMENTS

| 3,964,830 | 6/1976 | Ikdea et al. | 356/239 |
| 3,977,789 | 8/1976 | Hunter et al. | 356/239 |
| 3,988,068 | 10/1976 | Sprague | 356/239 |

Primary Examiner—David C. Nelms
Assistant Examiner—Khaled Shami
Attorney, Agent, or Firm—Spencer & Frank

[57] ABSTRACT

A method for testing components of transparent material for surface irregularities and occlusions, comprising the steps of dot-scanning the component by moving a light ray completely therethrough; detecting the light which represents flaws in at least the front and back surfaces of the component by receivers located on one side of the component; generating fault signals based on the light detected in the detecting step; digitizing the fault signals which are generated in the generating step; feeding the digitized signal to a mapped memory; and analyzing the signal by: (a) feeding the digitized signal to a number of sector counters via a preselectable number of thresholds; (b) evaluating the sector counters on-line according to preselected criterion regarding the number, location and gray tone distribution of the digitized fault signals; and (c) evaluating the signals in the mapped memory in a computer if the fulfillment of the criterion for evaluation of the sector counters cannot be sufficiently assured.

10 Claims, 2 Drawing Sheets

METHOD FOR TESTING COMPONENTS OF TRANSPARENT MATERIAL FOR SURFACE IRREGULARITIES AND OCCLUSIONS

BACKGROUND OF THE INVENTION

The invention in question concerns a method for testing components of transparent material for surface irregularities and occlusions by dot-scanning the component by a light ray and detecting the light which is deflected by the surface irregularities or occlusions.

Components of transparent material, for example optical or ophthalmic lenses, must be tested for flaws prior to their utilization, particularly for surface flaws such as scratches, smears, cracks, chipping, stains, and for occlusions such as bubbles or streaks. Such flaws would limit the usability of a lens if these were to exceed the limit values stated in DIN 3140.

DISCUSSION OF THE PRIOR ART

Conventionally, the testing of optical components is carried out by personnel in the form of visual inspection. Such a test must be performed to a large extent in a darkened room. It is expensive, not sufficiently objective and, due to the high degree of monotony of the testing procedure, not sufficiently reliable.

Efforts have, therefore, been made to develop methods and devices for automatic, objective testing of optical components.

From DE-OS No. 32 37 511, the method of placing optical components to be tested in the optical beam path of a television camera and of displaying through the component a test pattern on the camera is known. The disturbances caused by flaws in the component, produce a video signal which deviates from the control signal not influenced by the component. The flaw is deduced on the basis of the deviation between the control and actual signal. A device acting on this principle is rather expensive and is not able to detect smaller flaws, for example, those resulting from scratches, smears or hair-line cracks.

In order to increase the sensitivity of the testing procedure, it is recommended in DE-OS No. 30 11 014 that the component to be tested be illuminated completely, a television image be produced, and the video signal be analyzed line for line. This method is also not sufficiently exact.

An even older recommendation for a test method is to be found in DE-OS No. 23 37 597. According to this, a light ray is focused on the surface of the component to be tested and is punctiformly moved over the surface, at the same time being kept in focus. The light penetrating the component is reflected backwards, passes through the component again, and then falls onto a detector. Deviations in the intensity of the receiver signal make it possible to deduce a flaw and also to localize this flaw. A device acting on this principle is very expensive. It only allows those parts of the work-piece to be tested onto which the scanner ray is focused.

SUMMARY OF THE INVENTION

It is the object of the present invention to create a method for testing components of transparent material for surface irregularities and occlusions, which makes possible a speedy and reliable evaluation and classification of a component according to preselectable criteria, whereby both surfaces of the component are instrumental in the evaluation.

This assignment is solved by a method which comprises the steps of dot-scanning the component by moving a light ray completely therethrough; detecting the light which represents flaws in at least the front and back surfaces of the component by receivers located on one side of the component; generating fault signals based on the light detected in the detecting step; digitizing the fault signals which are generated in the generating step; feeding the digitized signal to a mapped memory; and analyzing the signal by: (a) feeding the digitized signal to a number of sector counters via a preselectable number of thresholds; (b) evaluating the sector counters on-line according to preselected criterion regarding the number, location and gray tone distribution of the digitized fault signals; and (c) evaluating the signals in the mapped memory in a computer if the fulfillment of the criterion for evaluation of the sector counters cannot be sufficiently assured.

With the method in accordance with the invention, a light section is produced through the component to be tested and moved completely through this. A device for generating such a light section is described in the patent application P No. 3621008.1 with the title "Device for Illuminating Components of Transparent Material in Testing for Irregularities", which was submitted by the Applicant on June 14, 1986, which application corresponds to U.S. patent application Ser. No. 062,182 filed June 15, 1987. The light section moved through the component to be tested, enables signals to be generated which are attributable to isotropicly diffusing flaws in the component and which are detected according to whether the front or back surface is involved. Flaws which diffuse anisotropicly can also be detected, whereby, however, differentiation between the front and back surface of the component is, in general, not possible.

A device for generating such signals is the subject of patent applicaion P No. 3620129.4 with the title "Device for Testing Components of Transparent Material for Surface Irregularities and Occlusions", which was submitted by the Applicant on June 14, 1986, which application corresponds to U.S. application Ser. No. 062,183 filed June 15, 1987.

The signals triggered by flaws in the component are, with the method in accordance with the invention, after being digitized, not only real-time evaluated but also, if required, via a mapped memory. The evaluation criteria have been derived from DIN 3140. These evaluate number and location of the fault signals and, with the method in accordance with the invention, can also evaluate the gray tone distribution, since the measured diffused light intensity is proportional to the depth of the allocated flaw. For reasons of expediency, dot and line-type flaws in the component are evaluated separately.

The signals analyzed in accordance with the evaluation criteria which are deposited as software in an evaluation computer, are advantageously used to classify the evaluated component.

The evaluation criteria are designed to analyze the signals allocated to the front and back surfaces of the component. The pre-processing of signals allocated to the front and back of the component are advantageously averaged after the signals have been digitized.

The invention also can process signals allocated to anisotropicly diffusing flaws.

With the present invention it is also possible to simultaneously visualize on a monitor those surfaces of the component which are to be evaluated.

BRIEF DESCRIPTION OF THE DRAWINGS

On the basis of FIGS. 1 and 2 of the enclosed drawings, the process sequence of the invention will, in the following, be more closely described. In detail.

DESCRIPTION OF THE PREFERRED EMBODIMENTS

Figure 1:
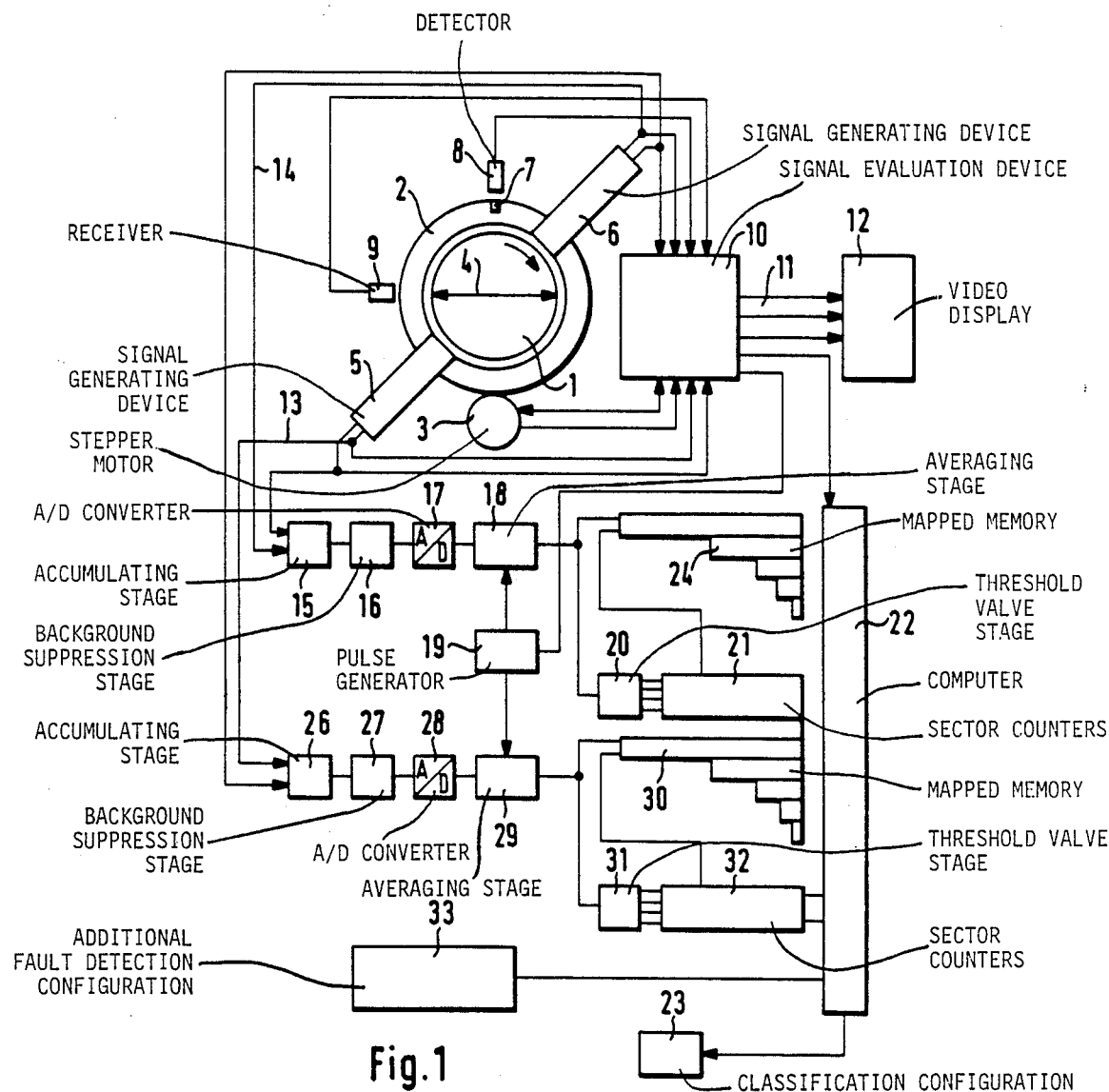
FIG. 1 shows one embodiment of a device for utilization of the method according to the invention.

In FIG. 1, a lens (1), which is placed on a rotary plate (2), turned in the direction of the arrow by means of a stepper motor (3), is depicted as the component to be tested. During this rotation, a light beam is moved linearly along a diameter in such a way that a light section (4) is produced through the lens (1). It is advantageous to employ a mirror scanner, which has not been illustrated here, to deflect the light beam.

Signal generating devices (5) and (6), generate output signals which are allocated to isotropicly diffusing flaws in the front and back surfaces of the lens (1). This type of device is described in more detail in the patent application P No. 3620129.4/U.S. application Ser. No. 062,183, supra.

The rotary plate (2) is provided with a mark (7), which is scanned by means of a detector (8). The signals generated by the detector (8), indicate in each case the commencement of a scanning cycle. A receiver (9) is provided for identification of the commencement of a scan line. The signals from the receivers (8) and (9), as well as the fault signals generated by the signal generating devices (5) and (6), are fed to a signal evaluation device (10), which is used for synchronization between the scanner and the stepper motor (3) and which produces, at its output (11), not only the video signal but also one proportional to the image dot pulse and one to the line pulse. These signals are fed to a video display (12), which produces an image of a selected surface of the lens (1) on a monitor.

The fault signals of both signal generating devices (5) and (6), corresponding to the front surface of the lens (1), are fed via the output lines (13) and (14) to an accumulating stage (15). From there, the aggregate signal reaches a stage (16) which is designed as a background suppression stage and which suppresses all signals below a specific gray scale value. The output signal of stage (16) is fed to an analog-to-digital converter (17). Here, the analog signal is, for instance, converted to a four-bit signal (16 gray levels).

When the lens (1) is scanned by means of the light section moved through this lens, each point of the surface of the lens (1) is scanned, in some cases repeatedly, dependent on its distance from the center. The extreme instance is the center itself, which, for example, when the rotation of the lens (1) is divided into 4096 steps, is scanned a total of 4096 times. It is, therefore, necessary to average the signals after stage (17). This type of averaging improves the signal-noise ratio and decreases susceptibility to interference. It is, in principle, possible to add up the multiply-recorded signal values and then to divide by the number of multiple scannings. Any other methods of averaging the signal may, of course, be used. Averaging is controlled via a signal from the pulse generator (19), which is itself synchronized by the signal evaluation device (10).

After the averaging stage (18), the signal is split. It is fed to a threshold value stage (20) for real-time evaluation, this stage splits the signal according to four adjustable digital thresholds. The split signals are fed to post-installed counters which are contained in sector counters (12). It has proven to be advantageous to provide a total of 64 sector counters. These divide the surface of the lens (1) into 64 angular sectors distributed uniformly over the surface.

At the completion of scanning, i.e. in the example mentioned, after 4096 angular steps in the rotation of the lens (1), there are, therefore, for each sector of the lens surface, four pixel totals. These pixel totals are dependent on the number, the location and the gray tone distribution of the fault signals.

The sector counters (21) are read out via a computer (22), which analyzes the result on the basis of the evaluation criteria derived from DIN 3140. The actual evaluation signal is at disposal at the output of the computer (22), and is fed to a classification configuration (23). This signal classifies the evaluated surface of the lens (1), whereby, for instance, two grades of classification are conceivable, namely lens good without reservation, or lens bad without reservation.

If classification into these rough grades is not possible, evaluation of the mapped memory (24) is carried out via the computer (22). This mapped memory (24) contains the signals supplied by stage (18), and, in problematical cases, enables the lens (1) to be analyzed according to more precise selection criteria without the lens having to be re-scanned. The evaluation of the mapped memory (24) is simplified, in that the sector counter (21) supplies address signals to the mapped memory (24), i.e. those sectors in which a more precise analysis must be performed are already preselected.

The evaluation of the front and back of the lens (1) is performed in parallel.

The fault signals proportional to the flaws on the back of the lens (1) are fed from the facilities (5) and (6) via the output lines (13) and (14), to an accumulating stage (26). This is again a background suppression stage (27) and is post-installed to an analog-to-digital converter (28). An averaging stage (29), is synchronized via the pulse generator (19). The output signals of stage (29) are fed in parallel to a mapped memory (30) and a threshold value stage (31) with post-installed sector counters (32). The actual evaluation of the signals is exactly as described in the aforegoing in conjunction with the front surface of the lens.

An additional fault detection configuration 33 supplies further lens (1) fault signals, for example, signals tripped by anisotropicly diffusing lens flaws. These signals are also analyzed in the computer (22) on the basis of the evaluation criteria already mentioned, and contribute to classification of the signals availabe in the classification configuration (23).

Figure 2:
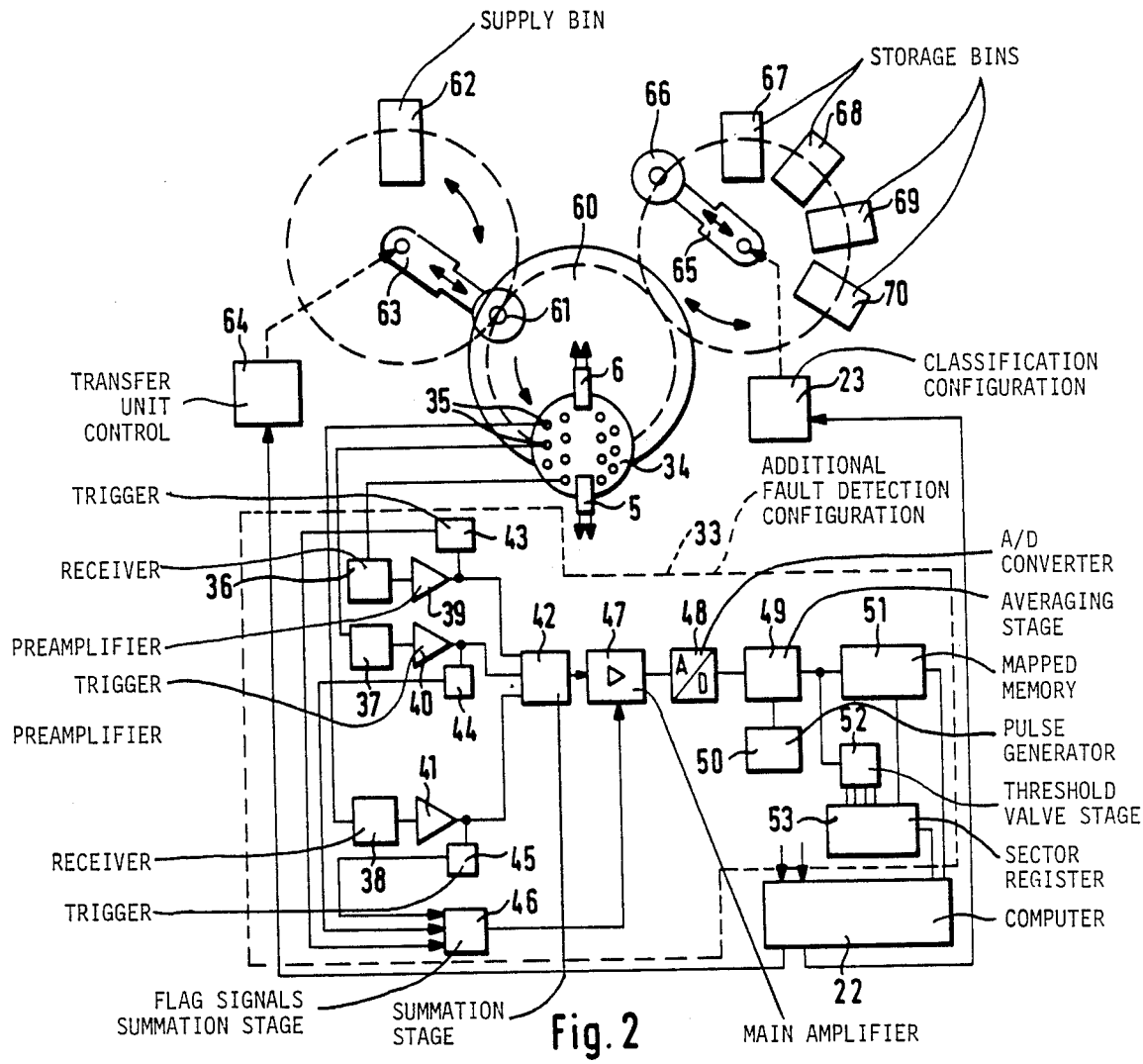
FIG. 2 shows a further embodiment of such a device.

FIG. 2 illustrates the additional fault detection configuration 33 (in more detail) for generation of fault signals attributable to anisotropicly diffusing lens flaws. A hemispherical shell (34) for detecting these signals, is arranged above the lens to be evaluated, being equipped not only with both signal generating devices (5) and (6) of the lens (1), but also with several receivers distributed over the surface. This type of device is more closely described in the patent application P NO. 3620129.4/U.S. application Ser. No. 062,183, supra.

In the illustration in FIG. 2, in order to maintain clarity, only a few of the installation openings in the hemispherical shell accommodating the receivers (36, 37, 38), which are separately described here, have been marked with (35). Each of these receivers is equipped with a preamplifier (39, 40, 41), the output signals of which are summated in a summation stage (42). The output signals of the preamplifiers pass simultaneously in each case to a trigger (43, 44, 45) and generate there a flag signal as soon as the output stage of the corresponding preamplifier produces a signal exceeding a preset threshold value. The appearance of such a flag signal is a sign that the respective receiver has received a fault signal. The flag signals are summated in stage (46), and the output signal of this stage is used to set the amplification factor of the main amplifier (47). In this way, the signal coming from stage (42) is amplified and at the same time scaled. This signal is converted in stage (48) into a digital signal, which is averaged in stage (49), this being controlled via the pulse generator (50). The average output signal of stage (49) is fed in parallel into a mapped memory (51) and via a threshold value stage (52), to a sector register (53). Evaluation of the fault signals supplied by the stages (51) and (53) is also as already described in conjunction with FIG. 1.

A configuration completely designed on the basis of digital technology is, of course, possible instead of the mixed analog-digital signal evaluation system described here.

In FIG. 2, a rotary plate is marked with (60), which, clock-actuated, moves the components to be evaluated (61) into the measuring position under the hemispherical shell. The components to be evaluated are stored in a supply bin (62) and are removed from this supply bin by means of a diagrammatically illustrated transfer unit (63) and placed on the rotary plate (60). A transfer unit control (64), which is controlled by the computer (22), controls the transfer unit (63).

After completion of scanning of the component (61) under the hemispherical shell (34), the computer (22) produces classification signals which are fed to a classification configuration (23). These classification characteristics identify the evaluation grade of the component analyzed. One of the evaluation grades is, for instance, that the component is good-without reservation. In this case, a signal is generated by the classification configuration (23) which moves the diagrammatically illustrated transfer unit (65) into a position in which is grasps the lens (66) which has just been evaluated, and deposits it in the storage bin (67). If the result of evaluation is that the lens (66) is, bad-without reservation then it is deposited by the transfer unit (65) in the storage bin (70). Various intermediate evaluation grades are possible, which can then be allocated to the storage bins (68) and (69).

The device in accordance with FIG. 2, therefore, automatically conveys lenses from a supply bin (62) into the measuring position, evaluates the fault signals from such a lens, analyzes these, and deposits the evaluated lens according to the evaluation grade determined, in one of the storage bins (67 to 70).

In FIG. 2, only one computer (22) is shown. In reality, process control is via a separate computer, whilst an evaluation computer is employed for actual evaluation of the measuring signals and calculation of the evaluation grades.

In summary, the present method allows for testing components of transparent material for surface irregularities and occlusions by using a linearly deflected light ray that produces a light section, which is completely moved through the component. During this movement, signals are generated which are, at least, allocated to the front and back surfaces of the component. These surface signals are digitized and fed in parallel in each case, both to a mapped memory and, via a preselectable number of thresholds, to a number of sector counters. These sector counters enable real-time evaluation of the fault signals according to a preselectable criterion in respect of the number, location and gray tone distribution. When this criterion is not sufficiently reliably fulfilled, i.e. in problematical cases, the fault signals stored in the mapped memory are automatically subsequently evaluated.

This method can be used to perform series-testing of optical components, whereby the components tested are classified into evaluation grades and deposited in corresponding containers.

We claim:

1. A method for testing components of transparent material for surface irregularities and occlusions, comprising the steps of:
   dot-scanning the component by moving a light ray which produces a light section in the component as the light ray passes completely therethrough;
   detecting the light which respresents surface irregularities and occlusions of at least the front and back surfaces of the component by receivers located on one side of the component;
   generating fault signals based on the light detected in said detecting step;
   digitizing the fault signals which are generated in said generating step;
   feeding the digitized signal to a mapped memory; and analyzing the signal by:
   (a) feeding the digitized signal through a preselectable number of thresholds to a number of sector counters;
   (b) evaluating the sector counters on-line according to preselected criterion regarding the number, location and gray tone distribution of the digitized fault signals; and
   (c) evaluating the signals in the mapped memory in a computer if the fulfillment of the criterion for evaluation of the sector counters cannot be sufficiently assured.

2. A method as defined in claim 1, further comprising the step of generating address signals by the sector counters for allocated sectors of the mapped memory.

3. A method as defined in claim 1, wherein said step of analyzing the signals is performed separately for the front surface and the back surface.

4. A method as defined in claim 1, further comprising the step of averaging the signals from surface elements of the component which are repeatedly scanned during the movement of light ray prior to said step of digitizing.

5. A method as defined in claim 1, further comprising the steps of:
   providing additional receivers for the detection of flaws in the component which diffuse anisotropicly;
   detecting the light from flaws in the component which diffuse anisotropicly;

generating additional fault signals based on light received by these additional receivers;

feeding the signals generated in said additional fault signal generating step by the additional receivers to a common main amplifier via respective preamplifiers;

immediately diverting a trigger signal from the signal of each preamplifier when the preamplifier signal has exceeded a predetermined threshold value;

adding all the respective trigger signals together;

controlling the amplification factor of the main amplifier by the aggregate signal produced in said adding step;

digitizing the aggregate signal produced in said adding step;

feeding the digitized aggregate signal to another mapped memory; and analyzing the aggregate signal.

6. A method as defined in claim 5, wherein said step of analyzing the aggregate signal comprises the steps of:

feeding the digitized aggregate signal to a further sector counter via a threshold value stage;

evaluating the further sector counter on-line according to preselected criterion regarding the number, location and gray tone distribution of the digitized aggregate fault signal; and evaluating the signals in the mapped memory in a computer if the fulfillment of the criterion for evaluation of the further sector counter cannot be sufficiently assured.

7. A method as defined in claim 5, further comprising the step of producing an image of a selected surface of the component by using the signals inputted to the computer.

8. A method as defined in claim 1, further comprising the step of producing an image of a selected surface of the component by using the signals inputted to the computer.

9. A method as defined in claim 1, further comprising the step of classifying the component based on the outcome from said step of analyzing.

10. A method as defined in claim 9, further comprising the step of controlling a transfer unit for placing the analyzed components into different storage bins.

* * * * *